US011426708B2

(12) United States Patent
Alsolami et al.

(10) Patent No.: US 11,426,708 B2
(45) Date of Patent: Aug. 30, 2022

(54) POTASSIUM-PROMOTED RED MUD AS A CATALYST FOR FORMING HYDROCARBONS FROM CARBON DIOXIDE

(71) Applicants: Saudi Arabian Oil Company, Dhahran (SA); King Abdullah University of Science and Technology, Thuwal (SA)

(72) Inventors: Bandar H. Alsolami, Dhahran (SA); Artem Russkikh, Thuwal (SA); Adrian Ramirez, Thuwal (SA); Genrikh Shterk, Thuwal (SA); Jorge Gascon, Thuwal (SA); Bandar A. Fadhel, Dhahran (SA)

(73) Assignees: King Abdullah University of Science and Technology, Thuwal (SA); Saudi Arabian Oil Compony, Dhahran (SA)

( * ) Notice: Subject to any disclaimer, the term of this patent is extended or adjusted under 35 U.S.C. 154(b) by 176 days.

(21) Appl. No.: 16/879,576

(22) Filed: May 20, 2020

(65) Prior Publication Data

US 2021/0268480 A1    Sep. 2, 2021

Related U.S. Application Data

(60) Provisional application No. 62/984,233, filed on Mar. 2, 2020.

(51) Int. Cl.
*B01J 21/06* (2006.01)
*B01J 37/02* (2006.01)
(Continued)

(52) U.S. Cl.
CPC ......... *B01J 21/063* (2013.01); *B01J 37/0201* (2013.01); *B01J 37/0236* (2013.01);
(Continued)

(58) Field of Classification Search
CPC . B01J 21/063; B01J 23/04; B01J 23/78; B01J 37/0201; B01J 37/0236; C10G 2/50;
(Continued)

(56) References Cited

U.S. PATENT DOCUMENTS 106,836 A    8/1870   Kuhlmann
665,346 A    1/1901   Reed
(Continued)

FOREIGN PATENT DOCUMENTS

CA    2938299    5/2015
CN    104923234  12/2017
(Continued)

OTHER PUBLICATIONS

PCT International Search Report and Written Opinion in International Appln. No. PCT/US2021/020408, dated May 20, 2021, 17 pages.
(Continued)

*Primary Examiner* — Brian A McCaig
(74) *Attorney, Agent, or Firm* — Fish & Richardson P.C.

(57) ABSTRACT

A method and catalyst for forming higher carbon number products from carbon dioxide is provided. An exemplary catalyst includes red mud including iron and aluminum, and impregnated potassium.

17 Claims, 9 Drawing Sheets

(51) Int. Cl.
    *C07C 11/04* (2006.01)
    *C07C 1/04* (2006.01)
    *C07C 11/08* (2006.01)

(52) U.S. Cl.
    CPC .............. *C07C 1/044* (2013.01); *C07C 11/04* (2013.01); *C07C 11/08* (2013.01); *C07C 2521/06* (2013.01)

(58) Field of Classification Search
    CPC ....... C07C 1/044; C07C 1/0445; C07C 11/04; C07C 11/08; C07C 2521/06; C07C 2523/04; C07C 2523/78; Y02P 20/00; C10K 3/026
    See application file for complete search history.

(56) References Cited

U.S. PATENT DOCUMENTS

| | | |
|---|---|---|
| 701,987 A | 6/1902 | Alz |
| 978,576 A | 12/1910 | Goodell |
| 2,378,905 A | 6/1945 | Bates |
| 2,614,066 A | 10/1952 | Cornell |
| 2,910,426 A | 10/1959 | Gluesenkamp |
| 3,288,692 A | 11/1966 | Leduc |
| 3,409,540 A | 11/1968 | Gould et al. |
| 3,427,235 A | 2/1969 | Leduc |
| 3,527,834 A | 9/1970 | Kehl et al. |
| 3,533,938 A | 10/1970 | Leas |
| 3,585,217 A | 6/1971 | Titzenthaler |
| 3,632,497 A | 1/1972 | Leduc |
| 3,702,292 A | 11/1972 | Burich |
| 3,726,789 A | 4/1973 | Kovach |
| 3,755,143 A | 8/1973 | Hosoi et al. |
| 3,856,659 A | 12/1974 | Owen |
| 3,894,059 A | 7/1975 | Selvaratnam |
| 4,064,062 A | 12/1977 | Yurko |
| 4,090,949 A | 5/1978 | Owen et al. |
| 4,119,507 A | 10/1978 | Simmrock et al. |
| 4,134,824 A | 1/1979 | Kamm et al. |
| 4,230,551 A | 10/1980 | Salyer et al. |
| 4,264,435 A | 4/1981 | Read et al. |
| 4,297,203 A | 10/1981 | Ford et al. |
| 4,310,501 A | 1/1982 | Reh et al. |
| 4,332,663 A | 6/1982 | Berneke |
| 4,426,276 A | 1/1984 | Dean et al. |
| 4,434,031 A | 2/1984 | Horowitz et al. |
| 4,522,802 A | 6/1985 | Setzer et al. |
| 4,527,003 A | 7/1985 | Okamoto et al. |
| 4,560,451 A | 12/1985 | Nielsen |
| 4,587,011 A | 5/1986 | Okamoto et al. |
| 4,602,986 A | 7/1986 | Ellis et al. |
| 4,655,904 A | 4/1987 | Okamoto et al. |
| 4,725,349 A | 2/1988 | Okamoto et al. |
| 4,735,728 A | 4/1988 | Wemhoff |
| 4,761,394 A | 8/1988 | Lauritzen |
| 4,786,400 A | 11/1988 | Farnsworth |
| 4,830,728 A | 5/1989 | Herbat et al. |
| 4,992,160 A | 2/1991 | Long et al. |
| 5,012,360 A | 4/1991 | Yamauchi et al. |
| 5,091,351 A | 2/1992 | Murakawa et al. |
| 5,108,581 A | 4/1992 | Aldridge |
| 5,344,849 A * | 9/1994 | Ayasse .................. C07C 1/0435 518/713 |
| 5,527,436 A | 6/1996 | Cooker et al. |
| 5,601,937 A | 2/1997 | Isenberg |
| 5,624,493 A | 4/1997 | Wagh et al. |
| 5,904,837 A | 5/1999 | Fujiyama |
| 5,906,728 A | 5/1999 | Iaccino et al. |
| 5,951,850 A | 9/1999 | Ino et al. |
| 6,033,555 A | 3/2000 | Chen et al. |
| 6,190,533 B1 | 2/2001 | Bradow et al. |
| 6,210,562 B1 | 4/2001 | Xie et al. |
| 6,280,593 B1 | 8/2001 | Wiese et al. |
| 6,293,979 B1 | 9/2001 | Choudhary et al. |
| 6,312,658 B1 | 11/2001 | Hufton et al. |
| 6,319,864 B1 | 11/2001 | Hannigan et al. |
| 6,336,791 B1 | 1/2002 | O'Toole |
| 6,531,515 B2 | 3/2003 | Moore, Jr. et al. |
| 6,656,346 B2 | 12/2003 | Ino et al. |
| 6,743,961 B2 | 6/2004 | Powers |
| 6,849,356 B2 | 2/2005 | Dow et al. |
| 6,979,757 B2 | 12/2005 | Powers |
| 7,019,187 B2 | 3/2006 | Powers |
| 7,045,554 B2 | 5/2006 | Raje et al. |
| 7,132,042 B2 | 11/2006 | Genetti et al. |
| 7,302,795 B2 | 12/2007 | Vetrovec |
| 7,374,664 B2 | 5/2008 | Powers |
| 7,378,561 B2 | 5/2008 | Olah et al. |
| 7,396,449 B2 | 7/2008 | Powers |
| 7,404,889 B1 | 7/2008 | Powers |
| 7,419,584 B2 | 9/2008 | Stell et al. |
| 7,460,333 B2 | 12/2008 | Akamatsu et al. |
| 7,550,642 B2 | 6/2009 | Powers |
| 7,592,290 B2 | 9/2009 | Hussain et al. |
| 7,642,292 B2 | 1/2010 | Severinsky |
| 7,744,747 B2 | 6/2010 | Halsey |
| 7,858,834 B2 | 12/2010 | Powers |
| 7,906,559 B2 | 3/2011 | Olah et al. |
| 7,972,498 B2 | 7/2011 | Buchanan et al. |
| 7,973,087 B2 | 7/2011 | Kibby et al. |
| 8,152,973 B2 | 4/2012 | Yamamoto et al. |
| 8,198,338 B2 | 6/2012 | Shulenberger et al. |
| 8,287,716 B2 | 10/2012 | Al-Sadah |
| 8,303,917 B2 | 11/2012 | Miyashiro et al. |
| 8,304,567 B2 | 11/2012 | Kadota et al. |
| 8,628,668 B2 | 1/2014 | Simonson |
| 8,816,137 B2 | 8/2014 | Olah et al. |
| 8,845,940 B2 | 9/2014 | Niven et al. |
| 8,951,333 B2 | 2/2015 | Cabourdin et al. |
| 9,085,497 B2 | 7/2015 | Jennings |
| 9,090,543 B2 | 7/2015 | Schoedel et al. |
| 9,096,806 B2 | 8/2015 | Abba et al. |
| 9,175,409 B2 | 11/2015 | Sivasankar et al. |
| 9,221,027 B2 | 12/2015 | Kuppler et al. |
| 9,242,230 B2 | 1/2016 | Moon et al. |
| 9,255,230 B2 | 2/2016 | Shafi et al. |
| 9,260,366 B2 | 2/2016 | Verhaak et al. |
| 9,279,088 B2 | 3/2016 | Shafi et al. |
| 9,284,497 B2 | 3/2016 | Bourane et al. |
| 9,284,502 B2 | 3/2016 | Bourane et al. |
| 9,296,961 B2 | 3/2016 | Shafi et al. |
| 9,303,323 B2 | 4/2016 | DiMascio et al. |
| 9,312,454 B2 | 4/2016 | Itoh et al. |
| 9,328,035 B1 | 5/2016 | Kuhn et al. |
| 9,435,404 B2 | 9/2016 | Goleski et al. |
| 9,555,367 B2 | 1/2017 | Masel et al. |
| 9,559,375 B2 | 1/2017 | Savinell et al. |
| 9,618,264 B1 | 4/2017 | Berdut-Teruel |
| 9,634,343 B2 | 4/2017 | Munier et al. |
| 9,675,979 B2 | 6/2017 | Hassell |
| 9,752,080 B2 | 9/2017 | Christensen et al. |
| 9,884,313 B2 | 2/2018 | Shen et al. |
| 9,963,392 B2 | 5/2018 | Deo et al. |
| 9,970,804 B2 | 5/2018 | Khousa et al. |
| 9,973,141 B2 | 5/2018 | Hammad et al. |
| 10,179,733 B2 | 1/2019 | Becker et al. |
| 10,252,243 B2 | 4/2019 | Fadhel et al. |
| 10,252,909 B2 | 4/2019 | Lofberg et al. |
| 10,329,676 B2 | 6/2019 | Kaczur et al. |
| 10,357,759 B2 | 7/2019 | D'Souza et al. |
| 10,422,754 B2 | 9/2019 | Al Hosani et al. |
| 2002/0156137 A1 * | 10/2002 | Zhou ....................... B01J 37/06 518/719 |
| 2005/0203194 A1 * | 9/2005 | Botes ................... B01J 35/0006 518/716 |
| 2005/0211603 A1 | 9/2005 | Guillaume et al. |
| 2006/0171065 A1 | 8/2006 | Akamatsu et al. |
| 2008/0011644 A1 | 1/2008 | Dean |
| 2008/0011645 A1 | 1/2008 | Dean |
| 2008/0015267 A1 * | 1/2008 | Lu ............................ C10G 2/33 518/718 |
| 2008/0083648 A1 | 4/2008 | Bishop et al. |
| 2008/0194900 A1 | 8/2008 | Bhirud |
| 2008/0277314 A1 | 11/2008 | Halsey |

(56) References Cited

U.S. PATENT DOCUMENTS

| | | | |
|---|---|---|---|
| 2008/0283445 | A1 | 11/2008 | Powers |
| 2009/0050523 | A1 | 2/2009 | Halsey |
| 2010/0089795 | A1 | 4/2010 | Fujiyama et al. |
| 2010/0137458 | A1 | 6/2010 | Erling |
| 2011/0083996 | A1 | 4/2011 | Shafi et al. |
| 2011/0132770 | A1 | 6/2011 | Sala et al. |
| 2011/0247500 | A1 | 10/2011 | Akhras et al. |
| 2013/0129610 | A1 | 5/2013 | Kale |
| 2013/0220884 | A1 | 8/2013 | Bourane et al. |
| 2013/0233766 | A1 | 9/2013 | Shafi et al. |
| 2013/0248419 | A1 | 9/2013 | Abba |
| 2015/0225295 | A1 | 8/2015 | Mcandlish et al. |
| 2015/0337445 | A1 | 11/2015 | Hasegawa et al. |
| 2015/0343416 | A1 | 12/2015 | Fadhel et al. |
| 2016/0002035 | A1 | 1/2016 | Ralston et al. |
| 2016/0038919 | A1 | 2/2016 | Landau et al. |
| 2016/0129423 | A1* | 5/2016 | Basset ............... C07C 2/76 423/651 |
| 2016/0264886 | A1 | 9/2016 | Davydov |
| 2016/0333487 | A1 | 11/2016 | Rodriguez |
| 2017/0050845 | A1 | 2/2017 | Lofberg et al. |
| 2017/0292197 | A1 | 10/2017 | Lei et al. |
| 2019/0194074 | A1 | 6/2019 | Amr et al. |
| 2019/0308183 | A1* | 10/2019 | Agblevor ............... C10G 3/62 |

FOREIGN PATENT DOCUMENTS

| | | |
|---|---|---|
| GB | 707987 | 4/1954 |
| WO | WO 2000009633 | 2/2000 |
| WO | WO 2009073436 | 6/2009 |
| WO | WO 2010009077 | 1/2010 |
| WO | WO 2010009082 | 1/2010 |
| WO | WO 2010009089 | 1/2010 |
| WO | WO 2010143783 | 12/2010 |
| WO | WO 2015128045 | 9/2013 |
| WO | WO 2014160168 | 10/2014 |
| WO | 104923234 | 9/2015 |
| WO | WO 2015183200 | 12/2015 |
| WO | WO 2016207892 | 12/2016 |
| WO | WO 2017130081 | 8/2017 |
| WO | WO 2019112555 | 6/2019 |

OTHER PUBLICATIONS

Das et al., "Exploring the Promotional Effects of K, Sr, and Mg on the Catalytic Stability of Red Mud for the Synthesis of Glycerol Carbonate from Renewable Glycerol," Industrial & Engineering Chemistry Research, Sep. 2019, 58(35): 15803-15817, 15 pages.

Russkikh et al., "Turning Waste into Value: Potassium-Promoted Red Mud as an Effective Catalyst for the Hydrogenation of $CO_2$," ChemSusChem, Wiley-VCH Verlag Deu, Apr. 2020, 13(11): 2981-2987, 7 pages.

"Hydrogen and Oxygen production via electrolysis powered by renewable energies to reduc environmental footprint of a WWTP.," Greenlysis, www.life-greenlysis.eu 2010-2012, 16 pages.

Albrecht et al., "Unexpectedly efficient $CO_2$ hydrogenation to higher hydrocarbons over non-doped $Fe_2O_3$," Appl. Catal., B, May 2017, 204: 119-126.

Bhuiyan, "Metathesis of Butene to Produce Propylene over Mesoporous Tungsten Oxide Catalyst: Synthesis, Characterization and Kinetic Modeling," Master thesis, King Fahd University of Petroleum and Minerals, Jun. 2013, 188 pages.

Chew et al., "Effect of nitrogen doping on the reducibility, activity and selectivity of carbon nanotube-supported iron catalysts applied in $CO_2$ hydrogenation," Appl. Catal., A, Jul. 2014, 482: 163-170.

Choi et al., "Carbon dioxide Fischer-Tropsch synthesis: A new path to carbon-neutral fuels," Appl. Catal., B, Mar. 2017, 202: 605-610.

Choi et al., "Hydrogenation of carbon dioxide over alumina supported Fe—K catalysts," Catalysis Letters, Mar. 1996, 40: 115-118.

Cowie et al., "Naturally occurring radioactive material and naturally occurring mercury assessment of black powder in sales gas pipelines," Radiation Protection and Environment, vol. 42, Issue 1 & 2, Jan.-Mar. & Apr.-Jun. 2019, 6 pages.

Crammer et al., "The Mechanism of Isomerization of Olefins with transition metal catalysts," Journal of the American Chemical Society, Mar. 1966, 88(15): 3534-3544.

Dinesh et al., "Iron-based flow batteries to store renewable energies," Environmental Chemistry Letters, Feb. 2018, 12 pages.

Ding et al., "CO2 Hydrogenation to Hydrocarbons over Iron-Based Catalyst: Effects of Physico-Chemical Properties of $Al_2O_3$ Supports," Ind. Eng. Chem. Res., 2014, 53(45): 17563-17569.

Du et al., "Sodium Hydroxide Production from Seawater Desalination Brine: Process Design and Energy Efficiency," Environ.Sci. Technol. 52, 5949-5958, 2018, 10 pages.

Godoy et al., "210Pb content in natural gas pipeline residues ("black-powder") and its correlation with the chemical composition," Journal of Environmental Radioactivity 83 (2005) 101e111, 12 pages.

Gräfe et al., "Bauxite residue issues: IV. Old obstacles and new pathways for in situ residue bioremediation," Hydrometallurgy, 2011, 108: 46-59.

Hu et al., "Hydrothermally stable MOFs for $CO_2$ hydrogenation over iron-based catalyst to light olefins," J. CO2 Util., 2016, 15, 89-95.

Hua et al., "Transformation of 2-Butene into Propene on $WO_3$/MCM-48: Metathesis and Isomerization of n-Butene," Catalysts, 2018, 8, 11 pages.

Lee et al., "Selective Positional Isomerization of 2-Butene over Alumina and La-promoted Alumina Catalysts," J. Ind. Eng. Chem., Dec. 2007, 13(7): 1062-1066.

Liu et al."Fe-MOF-derived highly active catalysts for carbon dioxide hydrogenation to valuable hydrocarbons," J. CO2 Util., Oct. 2017, 21:100-107.

Liu et al., "Pyrolyzing ZIF-8 to N-doped porous carbon facilitated by iron and potassium for $CO_2$ hydrogenation to value-added hydrocarbons," J. CO2 Util., May 2018, 25: 120-127.

Madadkhani, "Red mud as an Ironbased Catalyst for Catalytic Cracking of Naphthalene," Master's thesis, The University of British Columbia, 2014; Shiva Makadani, The University of British Columbia, Dec. 2016, 192 pages.

Morrison, "Cis-trans Isomerization of Olefins by Intramolecular Energy Transfer," Journal of the American Chemical Society, Feb. 1965, 87(4): 932.

Naik et al. "Carbon Dioxide sequestration in cementitious products," Report No. CNU-2009-02, REP-640, Collegef Engineering, University of Wisconsin-Milwaukee, Jan. 2009 53 pages.

Nam et al., "Catalytic conversion of carbon dioxide into hydrocarbons over iron supported on alkali ion-exchanged Y-zeolite catalysts," Appl. Catal., A, Apr. 1999, 179(1-2): 155-163.

Nam et al., "Catalytic Conversion of Carbon dioxide into hyrdrocarbons over zinc promoted iron catalysts," Energy onvers. Manage., 1997, 38: S397-S402.

Ndlela et al., "Reducibility of Potassium-Promoted Iron Oxide under Hydrogen Conditions," Ind. Eng. Chem. Res., 2003, 42: 2112-2121.

Numpilai et al., "Pore size effects on physicochemical properties of Fe—Co/K—$Al_2O_3$ catalysts and their catalytic activity in $CO_2$ hydrogenation to light olefins," Appl. Surf. Sci., Jul. 2019, 483, 581-592.

pall.com (online), "Cyclo-Filter System," retrieved from URL <https://www.pall.com/en/oil-gas/midstream/midstream-black-powder.html>, retrieved on Jun. 16, 2020, available on or before 2020, 4 pages.

Pavlov et al., "Processes of Synthesis of 1-Butene from 2-Butene by the Positional Isomerization on Suffocation Exchangers," Russian Journal of Applied Chemistry, Jul. 2009, 82(6): 1117-1122.

Ramirez et al., "Metal Organic Framework-Derived Iron Catalysts for the Direct Hydrogenation of $CO_2$ to Short Chain Olefins," ACS Catal., 2018, 8:9174-9182.

Russkikh et al., "Red mud as an efficient catalyst in turning $CO_2$ hydrogenation," Chemical Science Seminar, Oct. 13, 2019; Kaust, 2019, 1 page, Abstract only.

(56) References Cited

OTHER PUBLICATIONS shop.pall.com (online), "Black Powder Filter," retrieved from URL <https://shop.pall.com/us/en/search?SearchTerm=black+powder+filter&resetsearch=true>, retrieved on Jun. 16, 2020, available on or before 2020, 7 pages.

Thach et al., "Further Improvements in Isomerization of Olefins in Solvent-free conditions," Journal of Synthetic Communications, Nov. 1992, pp. 1379-1384, Abstract only.

Van Beurden, "On the Catalytic Aspects of Stream-Methane Reforming: A Literature Survey," ECN-I--04-003, retrieved from URL <https://publicaties.ecn.nl/PdfFetch.aspx?nr=ECN-I--04-003>, Dec. 2004, 27 pages.

Visconti et al., "$CO_2$ Hydrogentation to Lower Olefins on a High Surface Area K-Promoted Bulk FE-Catalyst," Appl. Catal., B 2017, 200, 530-542, 44 pages.

Wahyudi et al., "Utilization of Modified Red Mud as a Heterogeneous Base Catalyst for A26Transesterification of Canola Oil," Journal of Chemical Engineering of Japan, 2017, 50(7): 561-567.

Wang et al., "Fe—Cu Bimetallic Catalysts for Selective $CO_2$ Hydrogenation to Olefin-rich C2+ Hydrocarbons," Ind. Eng. Chem. Res., Feb. 2018, 57(13): 4535-4542.

Wei et al., "New insights into the effect of sodium on $Fe_3O_4$-based nanocatalysts for $CO_2$ hydrogenation to light olefins," Catal. Sci. Technol., 2016, 6(13): 4786-4793.

Yensen et al., "Open source all-iron battery for renewable energy storage," HardwareX 6 (2019) e00072, 2019, 11 pages.

You et al., "Hydrogenation of carbon dioxide to light olefins over non-supported iron catalyst," Chin. J. Catal., May 2013, 34(5): 956-963.

\* cited by examiner

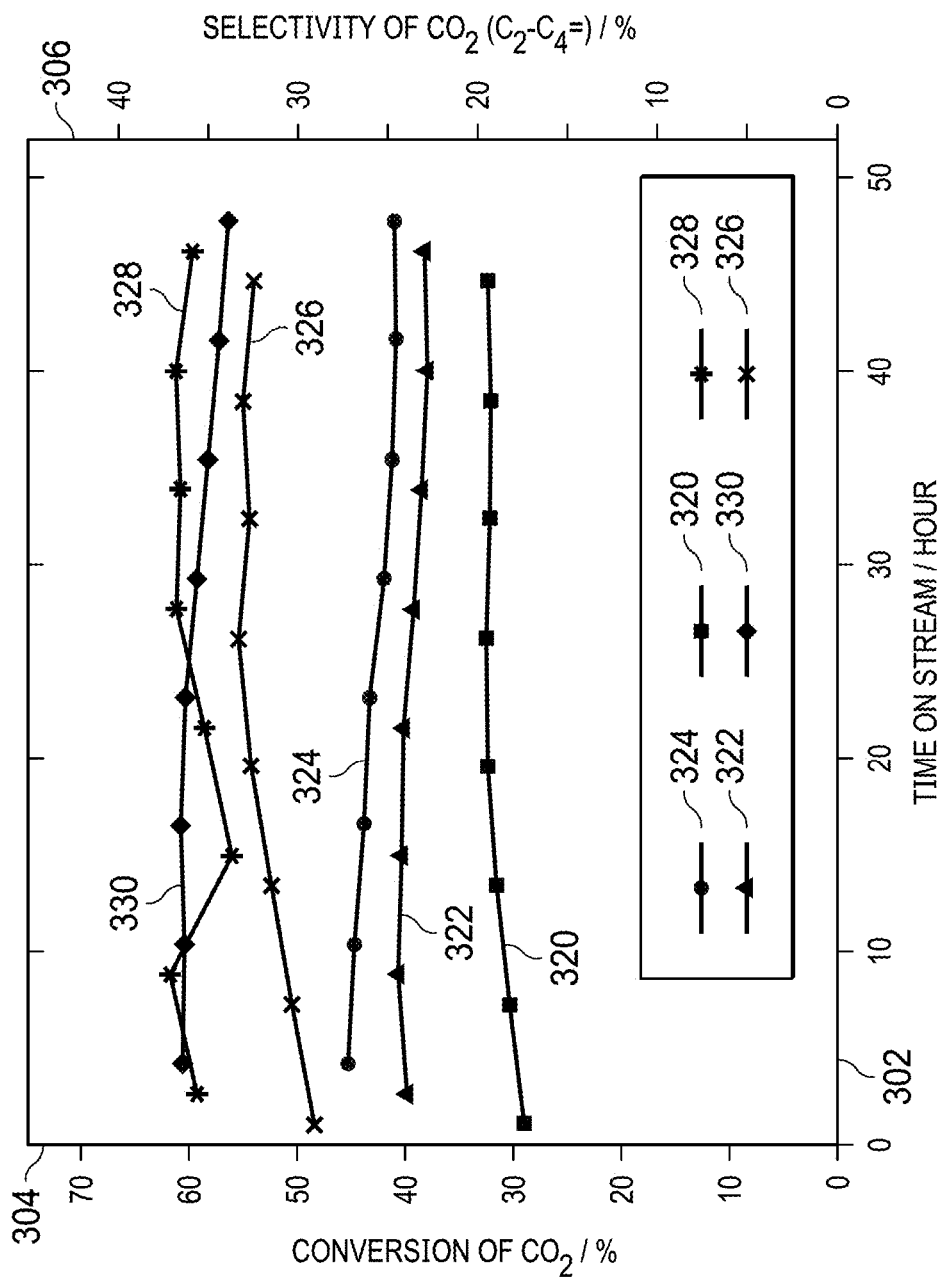

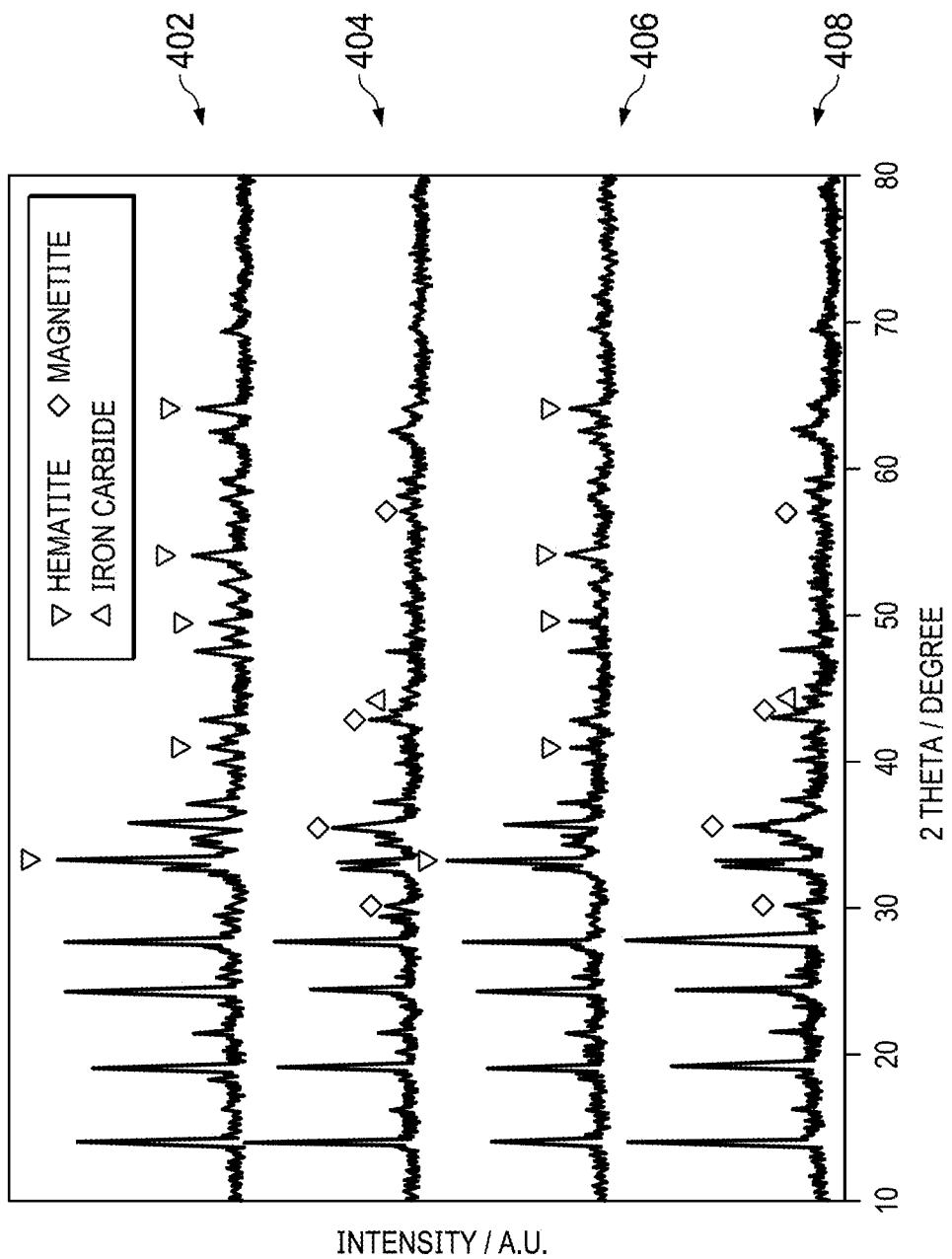

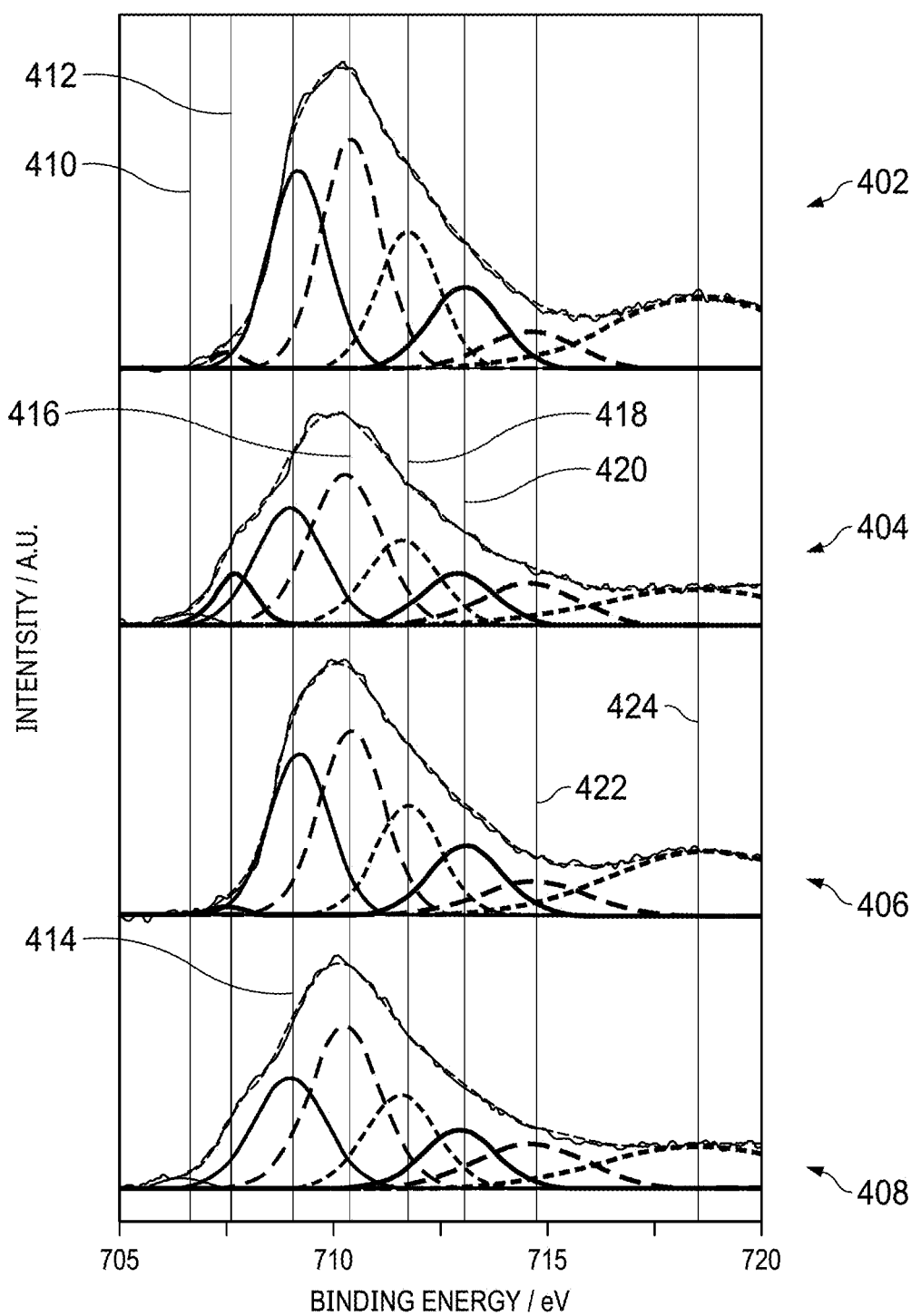

POTASSIUM-PROMOTED RED MUD AS A CATALYST FOR FORMING HYDROCARBONS FROM CARBON DIOXIDE

TECHNICAL FIELD

The present disclosure relates to the use of red mud as a catalyst.

BACKGROUND

With the constant world population growth, waste management has become a significant challenge. A special challenge for the scientific community is the storage of industrial hazardous wastes, such as red mud. Red mud is generated during alumina production in the Bayer process, which is responsible for more than 95% of all alumina produced in the world. In this process, for each ton of aluminum oxide produced, 0.3 to 2.5 tons of bauxite tailings, or red mud, are co-generated. As consequence, 155 million tons of red mud are being created annually with worldwide storage at over 3.5 billion tons in 2014. The typical disposal and storage methods for red mud are marine, lagooning, dry stacking and dry cake disposal. However, red mud solutions are highly alkaline, with a pH that ranges from 10 to 13. Further, red mud has a considerable metal content and, therefore, the potential leach into the soil represents a real danger for our environment.

SUMMARY

An embodiment described herein provides a method for using red mud as a catalyst for forming hydrocarbons from $CO_2$. The method includes impregnating red mud with potassium to create a potassium promoted catalyst and forming higher carbon number products from $CO_2$ using the potassium promoted catalyst.

Another embodiment described herein provides a catalyst for forming higher carbon number products from $CO_2$. The catalyst includes red mud including iron and aluminum, and impregnated potassium.

BRIEF DESCRIPTION OF DRAWINGS

FIGS. 3A-3D are plots showing the catalytic performance of red mud and potassium promoted red mud in the hydrogenation of $CO_2$.

FIGS. 4A-4C are plots showing the characterization of red mud and red mud promoted with 2% potassium after reaction at 350° C., 30 bar, and 50 hours in service.

DETAILED DESCRIPTION

Figure 1:
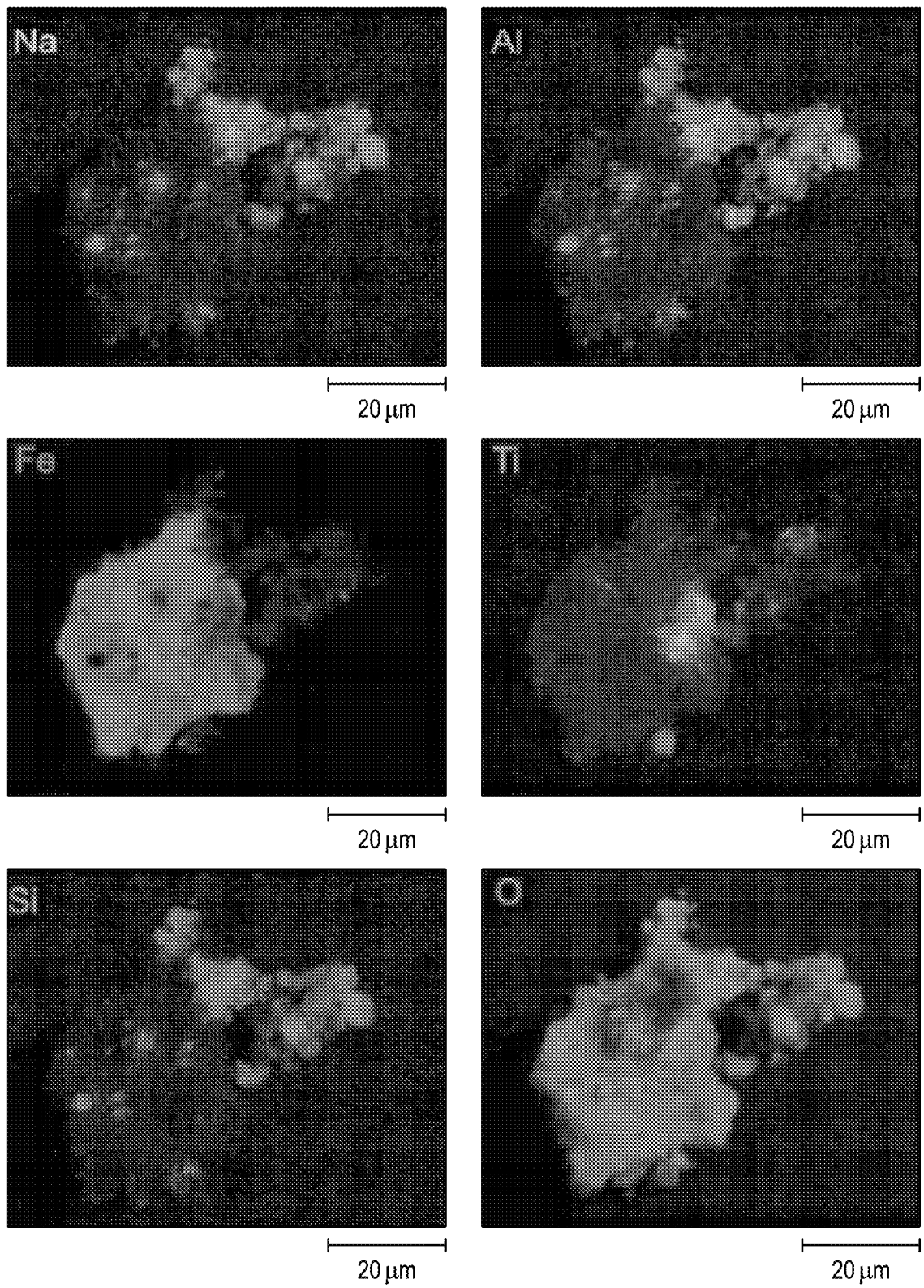
FIG. 1 is an elemental mapping of a red mud particle showing concentrations of six elements, as determined by EDS-SEM mapping.

The presence of different metals in red mud may enhance its use as a catalyst. The use of red mud (RM), or bauxite tailings, for reactions to fix $CO_2$ to form higher value products is described herein. Red mud may differ somewhat in composition depending on the location of the source. However, the compositional variations do not impact the use of red mud in the techniques described herein, as the basic catalytic components, e.g., iron oxide and alumina, among others, remain the same.

The use of red mud as a catalyst for $CO_2$ reactions allows the conversion of two wastes into higher value products. Generally, two different thermocatalytic routes have been proposed to convert $CO_2$ into higher value products. The $CO_2$ can be hydrogenated into methanol that can be further converted to olefins or aromatics over a zeolite in a bifunctional configuration. Alternatively, the $CO_2$ can be reacted with $H_2$ over an iron-based catalyst to form CO and $H_2O$, via a reverse water-gas shift reaction (RWGS). The CO can be further reacted with $H_2$ in a Fischer-Tropsch (FTS) process for conversion into a variety of higher carbon number hydrocarbons, such as light olefins ($C_2$-$C_4$), among others.

The main advantage of the RWGS/FTS reactions is the low undesired CO selectivity coupled with the large range of hydrocarbons that can be obtained. Catalysts that are promoted with potassium to increase selectivity for light olefins are especially useful. Targeting this fraction is economically favorable as light olefins demand is expected to increase.

In the techniques described herein, the red mud is potassium promoted, creating an efficient catalyst for the conversion of $CO_2$ to higher value products. As described with respect to the examples, the potassium-promoted red mud achieved a 45% conversion of $CO_2$ with a selectivity for light olefins ($C_2$-$C_4$) of 36% at 350° C., 30 bar and at 9600 $mL \cdot g^{-1} \cdot h^{-1}$, matching the performance of some of the best catalysts reported to date. As used herein, with respect to the $CO_2$ and CO, hydrocarbons with higher numbers of carbon atoms, such as $C_2$-$C_4$ olefins and $C_5^+$ compounds are higher carbon number products. Further, the potassium promoted catalyst does not have to be sintered before use.

EXAMPLES

The red mud sample described here in was provided by Saudi Aramco. Samples with 0.5, 1.0, 2.0 wt. % of potassium were prepared by the incipient wetness impregnation with potassium carbonate ($K_2CO_3$ from Aldrich, 99.9%) or potassium hydroxide (KOH from Aldrich, 99.9%) solutions. In a typical synthesis, 170 mg of red mud and the appropriate amount of potassium precursor were mixed in 0.7 mL of deionized in a 25 mL round-bottom flask. Then, the flask with the solution was connected to a rotatory evaporator at 90 rpm rate under 200 mbar pressure and 70° C. for 60 minutes. After evaporation, samples were dried in the oven using a heating rate of 5° $C. \cdot min^{-1}$ until 100° C. and hold at this temperature for 12 h.

Elemental analyses were performed by X-ray Fluorescence (XRF) analysis. The XRF analysis was performed on a Horiba® XGT-7200. The X-ray tube is equipped with an Rh target, voltage was set at 30 kV, no X-ray filter was used, and analysis preset time was 400 s. Before measurement, samples were placed on a double-sized tape (NICETACK™, Prod. No NW-15) and then placed in the chamber, which was then degassed. An average of four measurements per sample were taken. The results for a typical sample of Saudi Arabian red mud, before and after potassium treatment (targeting 2 weight % potassium content), are shown in Table 1.

TABLE 1

Typical Elemental composition of Saudi
Arabian red mud in weight percent.

| Element | As sourced | K-promoted |
|---|---|---|
| C | 6.0 | 6.9 |
| O | 46.5 | 43.6 |
| F | 1.9 | 0.6 |
| Na | 5.9 | 13.3 |
| Mg | 0.2 | 0.1 |
| Al | 6.3 | 10.1 |
| Si | 4.1 | 7.6 |
| P | 1.4 | 0.0 |
| S | 0.1 | 0.4 |
| K | 0.0 | 2.3 |
| Ca | 17.7 | 2.4 |
| Ti | 3.6 | 3.0 |
| V | 0.4 | 0.1 |
| Mn | 1.3 | 0.1 |
| Fe | 4.8 | 9.4 |
| Total | 100.0 | 100.0 |

Scanning Electron Microscopy (SEM) was performed on a FEI® Teneo VS microscope in the optiplan mode using the Everhart-Thornley detector. Samples were placed on a double-sided carbon tape (PELCO Tabs™, Prod. No 16084-1) on the aluminum stub prior to SEM characterization. No additional coating was applied. Distance of beam gun to sample was maintained at 10 mm. Accelerating voltage and beam current were set to 5 kV and 50 pA correspondingly.

Energy-Dispersive X-ray Spectroscopy (EDS) analysis was done by using a TEAM™ EDS analysis system provided by EDAX® at 20 or 30 kV and 3.2 or 13 nA current. Distance of beam gun to sample was 10 mm. Samples' drift was less than 2% during EDS sessions. Dead time was in the 30-40% range.

X-ray Diffraction Spectroscopy (XRD) was performed on a Brucker® D8 Advance. The source of X-ray radiation was CuKα and the analysis was performed in a 2θ range was from 10 to 80°. X-ray voltage was set to 40 kV, current was 40 mA. The crystalline phase was identified by comparison with Powder Diffraction File™ (PDF®), from the International Center for Diffraction Data. Elimination of fluorescence and Kβ radiation was done by using a LYNXEYE XE-T detector.

Transmission Electron Microscopy (TEM) was conducted on a FEI® Tecnai Twin microscope in the bright field mode. Prior to study, samples were grinded and sonicated in ethanol, then 2 μL of its solution was put on the carbon film (Electron Microscopy Sciences®, Prod. FCF400-CU). Filament voltage was set to 120 kV.

Nitrogen physisorption at 77 K was conducted on a Micrometrics® ASAP 2420 analysis system. Samples were degassed to 67 Pa at 1330 Pa·s$^{-1}$ rate, then held for 60 min. Following the hold, a temperature ramp was performed at a 10° C.·min$^{-1}$ rate until 300° C., then the temperature was held for 12 h. The volumetric $N_2$ adsorption/desorption isotherm was measured between $p \cdot (p^0)^{-1}$=0.01-0.95. BET surface area was calculated between p to $p^0$ ratio in 0.05-0.30 range.

Catalytic tests were conducted in a 16 channel Flowrence® Avantium setup. The reactors are standard steel with an inner diameter of 2.3 mm. Typically, 50 mg of catalyst were used per reactor. The reaction feed had 72% of $H_2$, 24% of $CO_2$ and 4% of He as a standard. The ratio between gas flow and mass of catalyst was maintained at 9600 mL·g$_1^{-1}$·h$^{-1}$ per channel. One of the 16 channels was used without catalyst as blank. The reaction was studied at 325° C., 350° C. and 375° C., while the pressure was maintained at 30 bar. Prior to feeding the reaction mixture all samples were pretreated in situ with a pure $H_2$ atmosphere for 4 hours at 350° C. After that, the tubes were pressurized using a membrane-based pressure controller.

Conversion (X, %), selectivities (S, %), and space time yields (STY, mmol·gcat$^{-1}$·h$^{-1}$) were calculated using the following formulas, respectively:

$$X(CO_2) = \left(1 - \frac{C(He_{blank}) \cdot C(CO_{2R})}{C(He_R) \cdot C(CO_{2blank})}\right) \cdot 100$$

$$S(C_n) = \frac{n \cdot C(C_n)}{\sum_x (n \cdot C(C_n))} \cdot 100$$

$$STY(C_nH_m) = \frac{x(CO_2) \cdot S(C_nH_m) \cdot SV \cdot 0.24}{22.4} \cdot \frac{1}{10000}$$

where $C(He_{blank})$, $C(CO_{2R})$, $C(He_R)$, $C(CO_{2blank})$ are the concentrations of the He in the blank reactor, $CO_2$ in the outlet of the reactor, He in the outlet of the reactor and $CO_2$ in the blank one determined by GC analysis respectively. The term $C(C_n)$ is the concentration of the product with n carbon atoms in the reactor outlet determined by GC analysis, x is the total number of all analyzed products. The term SV is the space velocity calculated in mL·gcat$^{-1}$·h$^{-1}$, and 0.24 molar concentration of the $CO_2$ in the blank reactor. The error found in carbon balance was smaller than 2.5% in every case.

The surface chemical composition of the powder samples was analyzed using high resolution X-ray Photoelectron Spectroscopy (XPS) on a Kratos Axis Ultra DLD spectrometer equipped with a monochromatic AlKα X-ray source (hν=1486.71 eV) operating at 150 W, under ultra-high vacuum (~10$^{-9}$ mbar). Measurements were performed in hybrid mode using electrostatic lenses, and the take-off angle was 0°. All spectra were recorded using an aperture slot of 300×700 μm. The survey and high-resolution spectra were collected at fixed analyzer pass energies of 160 eV and 20 eV respectively. For charge neutralization source of the low energy electrons was applied. As a reference for spectrum calibration, the C1s peak with binding energy 285.0 eV was used. The data was analyzed using commercially available software, CasaXPS v.2.3.19.

Characterization of the Red Mud Sample

X-ray Fluorescence (XRF) analysis was performed to investigate the elemental composition of the red mud sample, as the composition may vary depending on the source. The results show that the red mud described herein contained 14.3 wt. % of Na, 15.0 wt. % of Al, 15.5 wt. % of Si, 0.8 wt. % of S, 0.1 wt. % of K, 2.1 wt. % of Ca, 3.6 wt. % of Ti and 6.4 wt. % of Fe. However, analysis of different areas shows a great heterogeneity within the sample, although the data are in range of the reported typical compositions. The high iron content confirms that red mud is a candidate catalyst for the hydrogenation of $CO_2$. Additionally, the presence of Na and traces of K can be beneficial for olefin production. Moreover, Ti can potentially improve catalytic performance of Fe in the FTS synthesis. Finally, the high content of Al in the sample shows the limitation of the Bayer process, with almost ⅙ of aluminum left unrefined.

Scanning Electron Microscopy (SEM) revealed highly roughened particles of 50 to 200 μm in size. The elemental distribution on these particles shows certain agreement with the XRF characterization, pointing out again to the heterogeneity of the sample.

FIG. 1 is an elemental mapping of a red mud particle showing concentrations of six elements, as determined by EDS-SEM mapping. In the elemental mappings, several segregated phases can be distinguished. These phases include phases containing Na, Si, Al, Fe, and Ti. As shown in one of the EDS-SEM maps, Oxygen is well distributed across whole particle.

Figure 2:
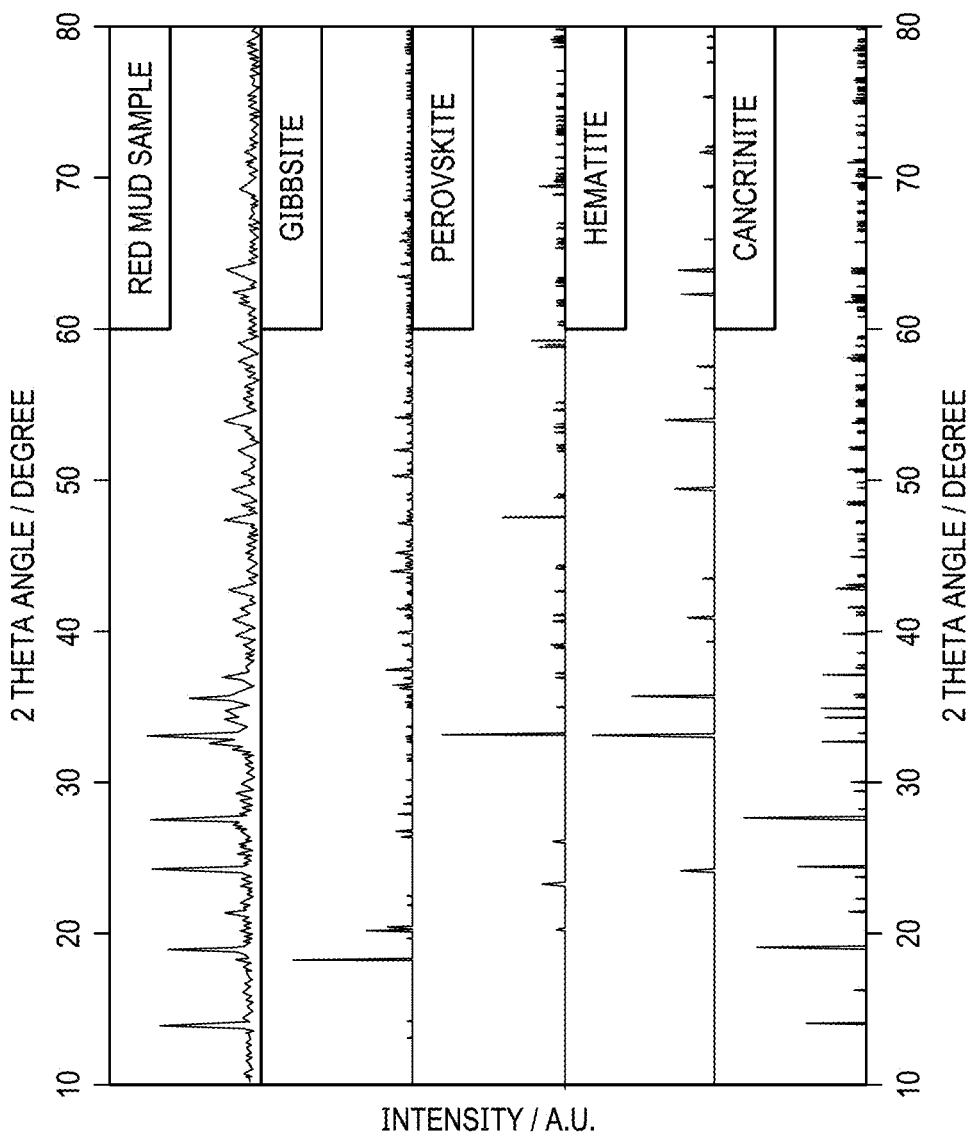
FIG. 2 is a comparison of the XRD diffractogram of red mud with simulated diffractograms of gibbsite, perovskite, hematite, and cancrinite.

FIG. 2 is a comparison of the XRD diffractogram of red mud with simulated diffractograms of gibbsite, perovskite, hematite, and cancrinite. Consistent with the SEM data, X-ray Diffraction Spectroscopy (XRD) revealed several crystalline phases: gibbsite ($Al(OH)_3$), perovskite ($CaTiO_3$), hematite ($Fe_2O_3$) and cancrinite (hydrate of carbonate and silicate of sodium, calcium and aluminum).

Transmission Electron Microscopy (TEM) showed the presence of particles with different sizes from around 10 to 80 nm and agglomerates with sizes from 500 nm to several μm. Nitrogen physisorption at 77 K of red mud revealed a type V isotherm with H3 hysteresis. The area of the red mud studied here was 12 $m^2 \cdot g^{-1}$, in line with other red mud measurements.

Red Mud as Catalyst for the Hydrogenation of $CO_2$

Figure 3A:
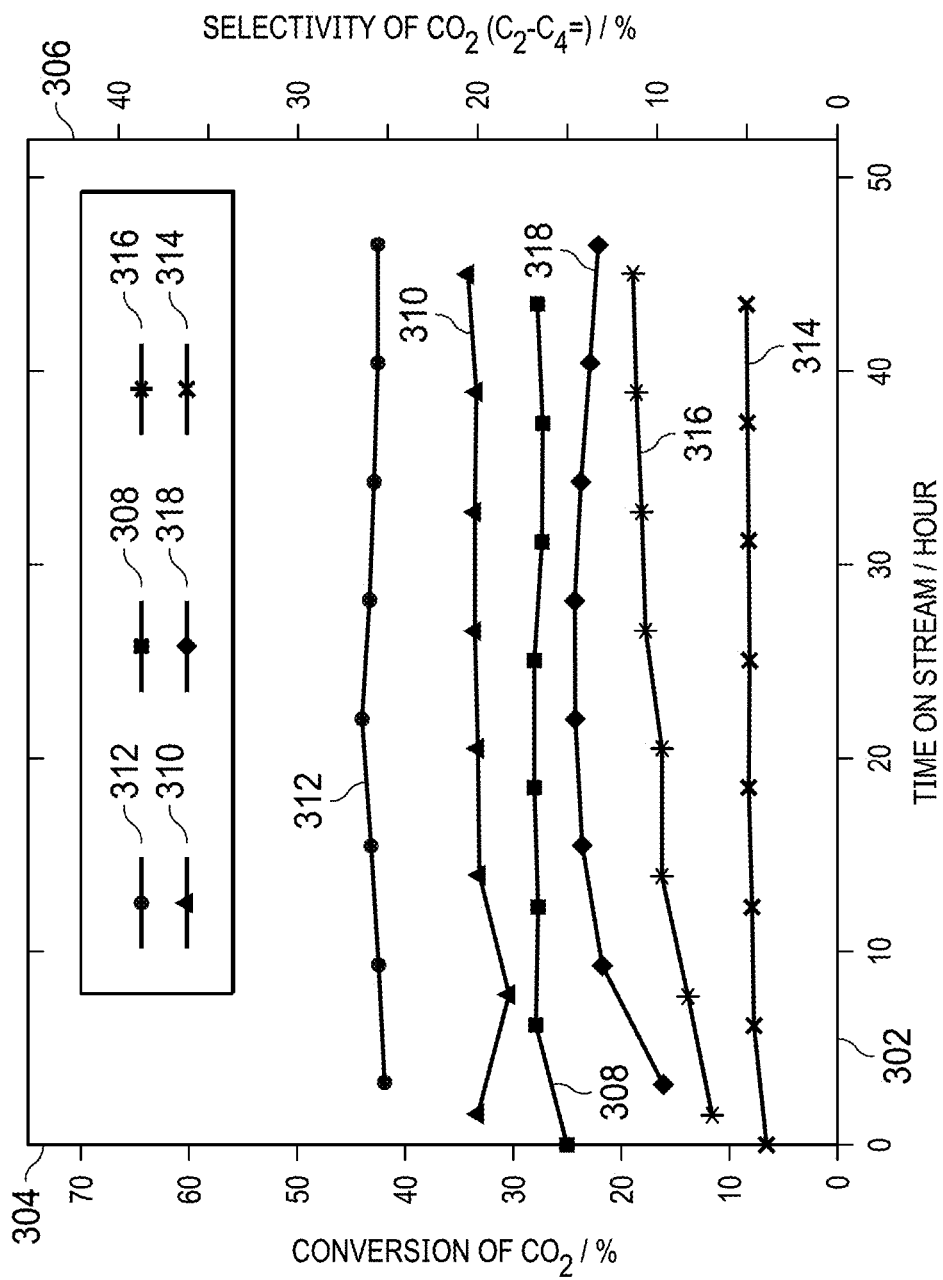

FIGS. 3A-3D are plots showing the catalytic performance of red mud and potassium promoted red mud in the hydrogenation of $CO_2$. FIG. 3A includes a series of plots against time (in hours) along the x-axis 302 showing the conversion of $CO_2$ (left y-axis 304) and selectivity to $C_2$-$C_4$ olefins (right y-axis 306) at 325° C., 350° C. and 375° C. for red mud. The conversion of $CO_2$ at 325° C. is shown as plot 308. At 350° C., the conversion of $CO_2$ is shown as plot 310. At 375° C., the conversion of $CO_2$ is shown as plot 312. The selectivity to $C_2$-$C_4$ olefins at 325° C. is shown as plot 314. At 350° C., the selectivity to $C_2$-$C_4$ olefins is shown as plot 316. At 375° C., the selectivity to $C_2$-$C_4$ olefins is shown as plot 318.

As expected from the above characterization, the unpromoted red mud is active in the hydrogenation of $CO_2$ at all the temperatures studied, especially at relatively high temperatures. Under the studied reaction conditions (30 bar, 9600 $mL \cdot g^{-1} \cdot h^{-1}$) raising the reaction temperature from 325° C. to 375° C. increased the conversion of $CO_2$ from 25% to 42% and the selectivity for $C_2$-$C_4$ olefins from 4% to 15%. This performance was stable during for at least 50 hours.

FIG. 3B includes a series of plots showing the conversion of $CO_2$ and selectivity to $C_2$-$C_4$ olefins at 325° C., 350° C. and 375° C. for red mud promoted with 2 wt. % of K from $K_2CO_3$. Like numbered items are as described with respect to FIG. 3A. Promotion with potassium substantially enhances the selectivity to olefins by favoring $CO_2$ adsorption and decreasing the hydrogenation strength of iron. The conversion of $CO_2$ at 325° C., using the potassium promoted red mud, is shown as plot 320. At 350° C., the conversion of $CO_2$ is shown as plot 322. At 375° C., the conversion of $CO_2$ is shown as plot 324. The selectivity to $C_2$-$C_4$ olefins at 325° C., using the potassium promoted red mud, is shown as plot 326. At 350° C., the selectivity to $C_2$-$C_4$ olefins is shown as plot 328. At 375° C., the selectivity to $C_2$-$C_4$ olefins is shown as plot 330.

After promotion, selectivity increases up to 36% at 350° C. Further, higher conversions are achieved (up to 45% at 375° C.) than without the potassium promotion, while catalyst stability remains unchanged.

Figure 3C:
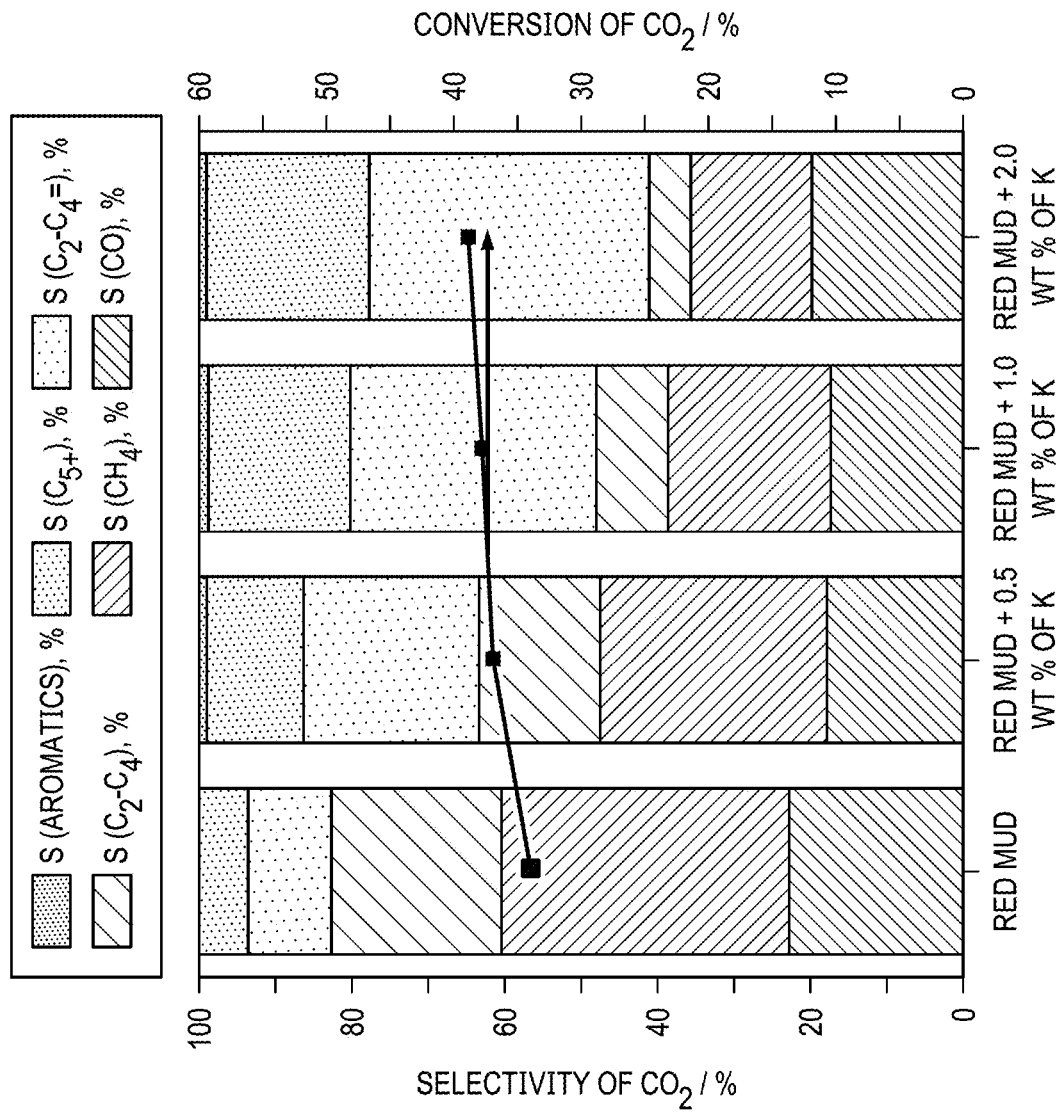

FIG. 3C is a bar chart of the product distribution for red mud and red mud promoted with potassium after 25 hours in service, showing the effects of potassium loading. After 25 hours on stream, at nearly isoconversion, selectivity to $C_2$-$C_4$ olefins increases from 15% for the unpromoted sample to 22%, 30% and 36% for samples containing 0.5, 1.0 and 2.0 wt % potassium correspondingly. In addition, increasing the potassium content also leads to an increase of the formation of higher hydrocarbons ($C_{5+}$). Thus, increasing the potassium content will lead to a decrease in the hydrogenation activity of Fe and therefore to the preference formation of olefins that may re-adsorb and allow for further chain growth.

Figure 3D:
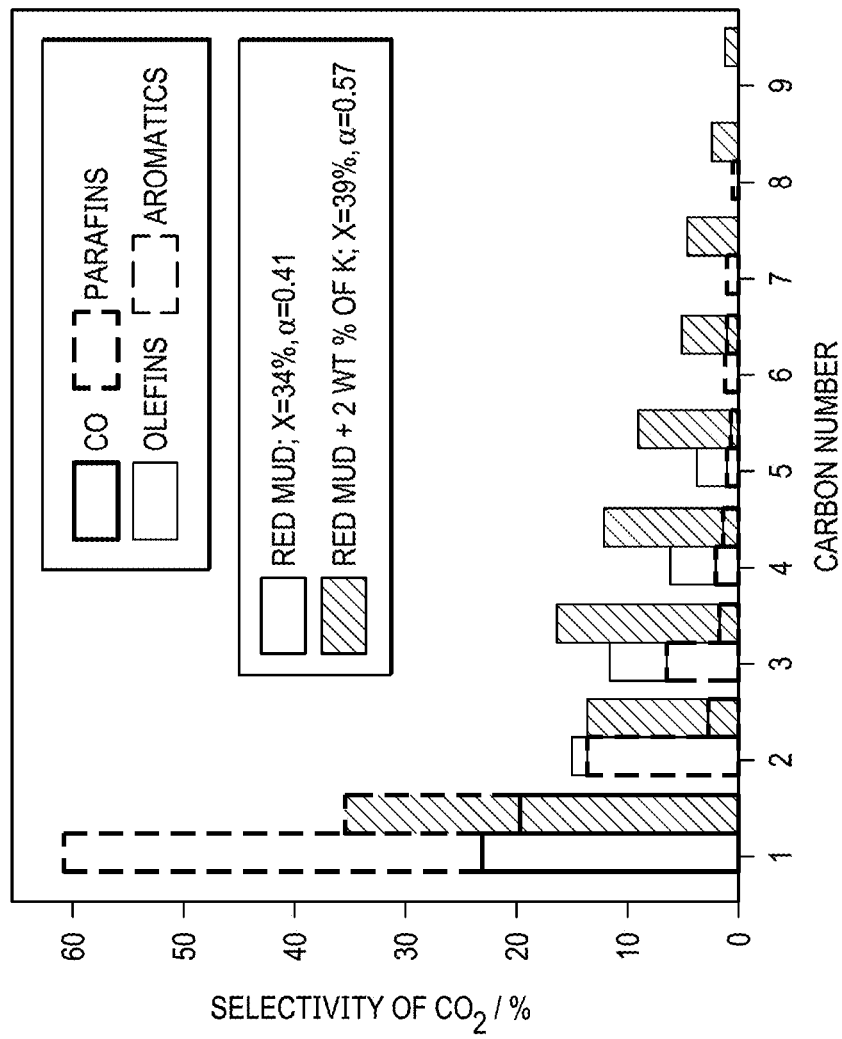

FIG. 3D is a bar chart of the detailed product distribution of the red mud and red mud promoted with 2 wt. % of potassium from $K_2CO_3$ after 25 h in service. The reaction was run at 350° C., 30 bar, $H_2/CO_2$=3, and 9600 $mL \cdot g^{-1} \cdot h^{-1}$.

Further, the type of potassium precursor may be investigated by comparing KOH and $K_2CO_3$ as promoters. While the data shows that the performance of both salts is very similar, $K_2CO_3$ shows a slightly better $C_2$-$C_4$ olefins selectivity at the same conversion level.

Figure 4B:
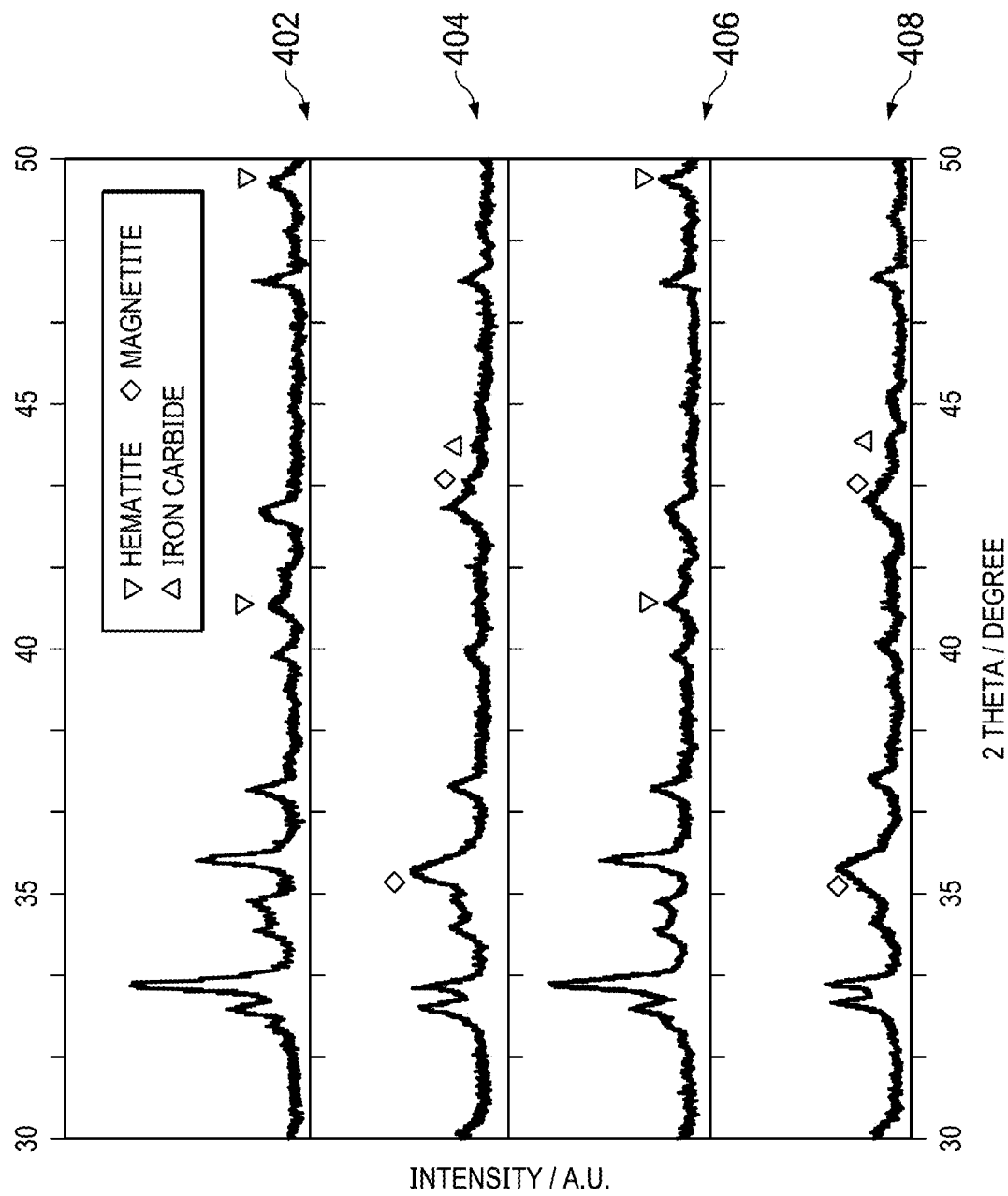

FIGS. 4A-4C are plots showing the characterization of red mud and red mud promoted with 2% potassium after reaction at 350° C., 30 bar, and 50 hours in service. FIG. 4A is a series of plots showing the XRD results of iron containing phases of samples before and after the catalytic reaction. The XRD results of the red mud before any reaction has taken place is shown in plot 402. The XRD results of the red mud after the reaction is shown in plot 404. The XRD results of the potassium treated red mud before the reaction is shown in plot 406. The XRD results of the potassium treated red mud after the reaction is shown in plot 408.

The XRD results after the reaction revealed that the iron partially reduces under reaction conditions, from $Fe^{III}$ to $Fe^{II}$. This reduction is accompanied with decreasing of peak intensities related to Hematite and increasing peak intensities related to Magnetite. To illustrate this point, sample diffractograms were used for Hematite, Magnetite, and iron carbide phases correspondingly.

FIG. 4B is a closer view of the 30° to 50° 2θ region. As shown in FIG. 4B, an iron carbide phase is also be found after reaction.

FIG. 4C is a comparison of XPS spectra before and after reaction. No significant differences were found in the phase distribution by comparing spectra of samples with and without K promotion. Further, as previously described, the content of iron carbide increases after reaction for both samples. In addition, red mud samples contain a variety of different Fe compounds, such as $Fe_3C$, $Fe_2O_3$, FeO, $K_2FeO_4$, and metallic iron, shown as overlapping peaks in the spectra of FIG. 4C. These peaks lie on intensity lines in the XRD spectra, where the peak for $Fe^0$ in each spectrum lies along line 410. The peak for $Fe_3C$ lies along line 412 in each spectrum. The peak for FeO lies along line 414 in each spectrum. The peak for $Fe_2O_3$ lies along line 416 in each spectrum. The peak for FeOOH lies along line 418 in each spectrum. The peak for $K_2FeO_4$ lies along line 420 in each spectrum. A satellite peak for $Fe^{II}$ lies along line 422 in each spectrum and a satellite peak for Fe' lies along line 424 in each spectrum. These peaks do not necessarily correspond to the amounts or presence of the $Fe^{II}$ or $Fe^{III}$ species. Similarly to the XRD, potassium promotion does not change the distribution of iron species according to XPS.

Following, TPR was performed on red mud and 2 wt % with K promoted red mud. Minor differences could be observed upon comparing both samples. For example, peaks below 120° C. were observed for the potassium promoted sample, which arise from the decomposition of $KHCO_3$ that starts at 67° C. Further, differences in the region from ~370°

C. to ~730° C. indicate the reduction of iron species, such as the reduction of Hematite ($Fe_2O_3$) into Magnetite ($Fe_3O_4$) at 420° C. (vs. 450° C. for the promoted sample); the broad reduction of Magnetite to iron monoxide from 510° C. to 720° C. (vs. from 530° C. to 730° C. for the promoted sample); and, further, the reduction to metallic Fe at 750° C. for both samples. The addition of potassium shifts reduction temperature of iron oxide species to higher temperatures. Unlike the metallic phase, these iron oxides are the active species for the RWGS reaction and, consequently, the first step is the formation of the carbides, which is the selective phase for the hydrocarbon formation in Fischer-Tropsch reaction. Accordingly, it can be concluded that the selective carbide phase formation takes place during the reaction, and that the main K effect is likely to be an electronic effect.

Last but not least, comparisons of the results for the catalysts discussed herein with the other iron based catalysts, as shown in Table 2, indicates that red mud outperforms most of them. As described here, red mud functions well as a catalyst for the conversion of $CO_2$ to olefins. Using a simple potassium promotion, 45% conversion of $CO_2$ with a light olefin ($C_2$-$C_4$) selectivity of 36% has been achieved at 375° C., 30 bar and at 9600 mL·$g^{-1}$·$h^{-1}$, matching the performance of some of the best catalysts reported to date.

aspect, the potassium promoted catalyst is used to facilitate a reaction between $CO_2$ and $H_2$ to form the higher carbon number products. In an aspect, the higher carbon number products comprise $C_2$-$C_4$ olefins.

In an aspect, the red mud is impregnated with potassium from potassium carbonate using an incipient wetness impregnation. In an aspect, the red mud is impregnated with potassium from potassium hydroxide using an incipient wetness impregnation.

In an aspect, the red mud is impregnated with a potassium precursor, and liquid water is evaporated from the impregnated red mud at an elevated temperature of about 70° C. The impregnated red mud is dried by placing the impregnated red mud and the heating device and ramping a temperature the heating device to a maximum temperature of between about 50° C. and about 200° C. at a rate of between about 0.5° C. per minute and about 20° C. per minute. The temperature is held at the maximum temperature for about 12 hours.

In an aspect, the potassium promoted catalyst provides an about 45% conversion of $CO_2$ with a selectivity for $C_2$-$C_4$ olefins of about 36% at a temperature of between about 300° C. and about 400° C., and 30 bar, and about 9600 mL per gram per hour.

TABLE 2

Comparison of the catalyst performance measured as conversion of $CO_2$, light olefin selectivity ($C_2$-$C_4$), and light olefins space-time yield (STY) of the promoted Red Mud catalyst and different Fe Fischer-Tropsch catalysts.

| Catalyst | T (° C.) | P (bar) | GHSV (mL · $gcat^{-1}$ · $h^{-1}$) | Conv. (%) | Sel $C_2$-$C_4$= (%) | STY ($mmol_{c2-c4=}$ · $gcat^{-1}$ · $h^{-1}$) |
|---|---|---|---|---|---|---|
| Red Mud + 2 wt % of K (CURRENT) | 375 | 30 | 9600 | 45 | 36 | 16.4 |
| Fe/$Al_2O_3$ | 400 | 30 | 1800 | 52 | 28 | 2.9 |
| ZIF-8/$Fe_2O_3$ | 300 | 30 | 3600 | 23 | 23 | 2.1 |
| K-Fe15 | 300 | 5 | 2700 | 45 | 37 | 5.1 |
| Fe—Zn | 300 | 10 | 1900 | 27 | 39 | 2.2 |
| $Fe_2O_3$_CT600 | 300 | 10 | 1140 | 23 | <27 | <0.7 |
| N—K-600-0 | 400 | 30 | 3600 | 43 | 27 | 4.7 |
| FeZnK—NC | 320 | 30 | 7200 | 35 | 32 | 9.0 |
| 1% B 5% K modified Fe | 340 | 20 | 1200 | 38 | 32 | 1.5 |
| $CuFeO_2$-12 | 300 | 10 | 1800 | 18 | 21 | <0.8 |
| Fe—K/$Al_2O_3$ K/Fe = 1.0 | 400 | 20 | 1900 | 68 | 42 | 6.0 |
| Fe/NCNT | 360 | 25 | 50000 | 25 | 2 | 3.0 |
| Fe/NaY | 300 | 10 | 1900 | 21 | 23 | 1.0 |
| FeNa(1.18) | 320 | 30 | 2000 | 41 | 39 | 3.4 |
| Fe—Cu(0.17)/K(1.0)/$Al_2O_3$ | 300 | 11 | 3600 | 29 | 6 | 0.7 |
| CL—$Al_2O_3$ | 320 | 20 | 9000 | 42 | 36 | 12.1 |
| K/Fe@NC-400 | 320 | 30 | 7200 | 31 | 33 | 8.2 |
| Fe/C + K(0.75) | 320 | 30 | 24000 | 36 | 33 | 31.8 |
| $Fe_2O_3$@$K_2CO_3$ | 350 | 30 | 10000 | 48 | 31 | 16.6 |

An embodiment described herein provides a method for using red mud as a catalyst for forming hydrocarbons from $CO_2$. The method includes impregnating red mud with potassium to create a potassium promoted catalyst and forming higher carbon number products from $CO_2$ using the potassium promoted catalyst.

In an aspect, the potassium promoted catalyst is used to facilitate a reverse water-gas shift reaction between $CO_2$ and hydrogen ($H_2$) to form carbon monoxide (CO) and water ($H_2O$). In an aspect, the potassium promoted catalyst is used to facilitate a Fisher-Tropsch reaction between the CO and the $H_2$ to form the higher carbon number products. In an In an aspect, the red mud is impregnated with potassium to a weight percent content of potassium of about 2%.

An embodiment of the present technique provides a method of making a reverse water gas shift/Fischer-Tropsch catalyst for forming higher carbon number products from $CO_2$, including impregnating red mud with potassium to form a potassium promoted catalyst.

In an aspect, the red mud is mixed with a potassium precursor in a water solution. In an aspect, the potassium precursor comprises potassium carbonate, or potassium hydroxide, or both. In an aspect, the method includes evaporating liquid water from the impregnated red mud at an elevated temperature of about 70° C. and drying the impregnated red mud. The red mud is dried by placing the impregnated red mud in a heating device, ramping a temperature of the heating device to a maximum temperature of between about 50° C. and about 200° C. at a rate of between about 0.5° C. per minute and about 20° C. per minute, and holding the temperature the maximum temperature for about 12 hours. In an aspect, the red mud is impregnated with the potassium to form the potassium promoted catalyst with and about 2 weight percent potassium.

Another embodiment described herein provides a catalyst for forming higher carbon number products from $CO_2$. The catalyst includes red mud including iron and aluminum, and impregnated potassium.

In an aspect, the catalyst includes 2 weight percent of impregnated potassium. In an aspect, the catalyst includes 0.5 weight % impregnated potassium, or 1.0 weight % impregnated potassium. In an aspect, the catalyst includes titanium.

In an aspect, the red mud includes gibbsite, perovskite, hematite, or cancrinite, or any combinations thereof. In an aspect, the red mud includes Saudi Arabian red mud.

Other implementations are also within the scope of the following claims.

What is claimed is:

1. A method for using red mud as a catalyst for forming hydrocarbons from carbon dioxide ($CO_2$), comprising:
   impregnating red mud with potassium to create a potassium promoted catalyst with about 2 weight % potassium;
   loading the potassium promoted catalyst in a reactor;
   passing a reaction feed through the reactor, wherein the reaction feed comprises $CO_2$ and hydrogen ($H_2$); and
   forming higher carbon number products in the reactor from the $CO_2$ and $H_2$ using the potassium promoted catalyst.

2. The method of claim 1, further comprising using the potassium promoted catalyst to facilitate a reverse water-gas shift reaction between $CO_2$ and hydrogen ($H_2$) to form carbon monoxide (CO) and water ($H_2O$).

3. The method of claim 2, further comprising using the potassium promoted catalyst to facilitate a Fischer-Tropsch reaction between the $CO_2$ and the $H_2$ to form the higher carbon number products.

4. The method of claim 1, wherein the higher carbon number products comprise $C_2$-$C_4$ olefins.

5. The method of claim 1, further comprising impregnating the red mud with potassium from potassium carbonate using an incipient wetness impregnation.

6. The method of claim 1, further comprising impregnating the red mud with potassium from potassium hydroxide using an incipient wetness impregnation.

7. The method of claim 1, further comprising:
   impregnating the red mud with a potassium precursor;
   evaporating liquid water from the impregnated red mud at an elevated temperature of about 70° C.; and
   further drying the impregnated red mud by:
   placing the impregnated red mud in a heating device;
   ramping a temperature of the heating device to a maximum temperature of between about 50° C. and about 200° C. at a rate of between about 0.5° C. per minute and about 20° C. per minute; and
   holding the temperature at the maximum temperature for about 12 hours.

8. The method of claim 1, wherein the potassium promoted catalyst provides an about 45% conversion of $CO_2$ with a selectivity for $C_2$-$C_4$ olefins of about 36% at a temperature of between about 300° C. and about 400° C., and 30 bar, and about 9600 mL per gram per hour.

9. A method of making a reverse water gas shift/Fischer-Tropsch catalyst for forming higher carbon number products from $CO_2$, comprising impregnating red mud with potassium to form a potassium promoted catalyst with about 2 weight % potassium.

10. The method of claim 9, further comprising mixing the red mud with a potassium precursor in a water solution.

11. The method of claim 10, wherein the potassium precursor comprises potassium carbonate, or potassium hydroxide, or both.

12. The method of claim 9, further comprising:
   evaporating liquid water from the impregnated red mud at an elevated temperature of about 70° C.; and
   further drying the impregnated red mud by:
   placing the impregnated red mud in a heating device;
   ramping a temperature of the heating device to a maximum temperature of between about 50° C. and about 200° C. at a rate of between about 0.5° C. per minute and about 20° C. per minute; and
   holding the temperature the maximum temperature for about 12 hours.

13. A catalyst for forming higher carbon number products from $CO_2$, comprising red mud comprising iron and aluminum, and impregnated potassium wherein the catalyst comprises about 2 weight % potassium.

14. The catalyst of claim 13, further comprising 0.5 weight % impregnated potassium, or 1.0 weight % impregnated potassium.

15. The catalyst of claim 13, comprising titanium.

16. The catalyst of claim 13, wherein the red mud comprises gibbsite, perovskite, hematite, or cancrinite, or any combinations thereof.

17. The catalyst of claim 13, wherein the red mud comprises Saudi Arabian red mud.

* * * * *